United States Patent [19]

Wang et al.

[11] 4,298,938

[45] Nov. 3, 1981

[54] BACKUP CONTROL CIRCUIT FOR KIDNEY DIALYSIS MACHINE

[75] Inventors: Cheng L. Wang; Charles Soodak, both of Silver Spring; David Lohr, Ellicott City, all of Md.

[73] Assignee: Baxter Travenol Laboratories, Inc., Deerfield, Ill.

[21] Appl. No.: 115,874

[22] Filed: Jan. 28, 1980

[51] Int. Cl.$^3$ ........................ B01D 13/00; G05D 7/06; G06G 7/57

[52] U.S. Cl. ............................ 364/413; 128/DIG. 3; 210/90; 371/14

[58] Field of Search ................................ 364/413–417; 371/14; 210/87, 90, 96.2; 128/214 E, DIG. 3, 13

[56] References Cited

U.S. PATENT DOCUMENTS

| | | | |
|---|---|---|---|
| 3,441,136 | 4/1969 | Serfass et al. | 210/96.2 X |
| 3,814,249 | 6/1974 | Eaton | 210/87 X |
| 4,060,485 | 11/1977 | Eaton | 210/87 |
| 4,148,314 | 4/1979 | Yin | 210/90 X |
| 4,153,554 | 5/1979 | Von Der Heide et al. | 210/96.2 X |

*Primary Examiner*—Felix D. Gruber
*Attorney, Agent, or Firm*—Robert A. Benziger; Thomas R. Vigil; Paul C. Flattery

[57] ABSTRACT

The backup control circuit is used with a main control circuit for a kidney dialysis machine and is operable upon failure of the main control circuit to operate with a predetermined time period to cause closing of a dialysate operate valve and opening of a dialysate bypass valve and/or stopping of a blood pump when an aberrant condition in the dialysate conductivity, temperature, flow or negative pressure are sensed and/or when an aberrant condition of the arterial or venous blood pressure is sensed and/or excessive leakage of blood into the dialysate is sensed. The backup control circuit includes control circuitry for controlling operation of the back-up control circuit, the circuitry having input contacts coupled to sensor inputs to the main control circuit. A time delay circuit has an input coupled to the control circuitry and is operable to initiate a timing cycle for the predetermined time period upon receiving an error signal from the control circuitry. Energizing and de-energizing circuitry has an input coupled to an output of the time delay circuit and outputs coupled to points in the main control circuit associated with coils for the dialysate operate valve, the dialysate bypass valve and the blood pump. The energizing and de-energizing circuitry is operable upon receiving an operate signal, after said predetermined time period has occurred and the main control circuit has not functioned properly, to close the operate valve, open the bypass valve and stop the blood pump.

4 Claims, 3 Drawing Figures

BACKUP CONTROL CIRCUIT FOR KIDNEY DIALYSIS MACHINE

BACKGROUND OF THE INVENTION

1. Field of the Invention

The present invention relates to control circuits for a kidney dialysis machine and more particularly to a backup control circuit connected to a main circuit for a modular proportioning kidney dialysis machine.

2. Description of the Prior Art

Heretofore there has been utilized in a modular proportioning kidney dialysis machine, a main control circuit which has inputs connected to various sensors which sense aberrant conditions in the dialysate and aberrant conditions in the arterial and venous blood pressure as well as an excess of blood leakage into the dialysate. More specifically, one sensor senses when the conductivity, temperature, flow and/or negative pressure of the dialysate is out of a predetermined range. When this occurs an error condition or alarm signal is generated which is utilized by the main control circuit to effect closing of a dialysate operate valve and opening of a dialysate bypass valve to bypass the dialysate around the kidney dialysis machine.

Another sensor senses when the arterial blood pressure and/or the venous blood pressure of the patient are outside of predetermined pressure ranges. When an aberrant or out of range condition occurs, an error or alarm signal is generated which is sensed by the main control circuit and utilized to stop operation of the blood pump.

Further, the waste dialysate from the kidney dialysis machine is passed by an optical sensor which senses the optical density of the dialysate to determine the amount of red blood cells leaking into the dialysate across a membrane in the kidney dialysis machine. When the amount of blood leakage exceeds a certain value indicating an aberrant operating condition, another error or alarm signal is generated which is sensed by the main control circuit to cause stopping of the blood pump.

The main control circuit also includes an override switch so that an operator, after noting the occurrence of an aberrant operating condition, can turn the blood pump back on to pump the patient's blood back into the patient. Also there is provided a purge switch, a clean switch, an interlock switch associated with the clean switch and a sterilize input for sensing a sterilize signal indicating that the kidney dialysis machine is to be purged and cleaned.

A main control circuit functioning in the manner described above has a number of components, which because of the number of components and because of the cost of components, are normal reliability components and not extra high reliability components. As a result, and although the failure rate of these components is very low, it is possible that a component failure could occur which would result in improper or malfunctioning of the main control circuit. More specifically, the main control circuit, because of a component failure, could conceivably fail to close the operate valve, open the bypass valve and/or stop the blood pump.

To ensure against such a possible failure of the main control circuit, the backup control circuit of the present invention utilizes extra high reliability components and is connected to the main control circuit in such a way as to take over operation of the control circuit in case there is a component failure in the main control circuit thereby to ensure proper closing of the operate valve, opening of the bypass valve, and stopping of the blood pump when an aberrant operating condition of the dialysate or blood is sensed.

The particular manner in which the backup control circuit functions to take over the operation of the main control circuit if the main control circuit does not operate within a predetermined time period after an aberrant condition is sensed, is more fully described hereinafter.

SUMMARY OF THE INVENTION

According to the invention there is provided a backup control circuit for use with a main control circuit for a kidney dialysis machine, said backup control circuit being operable upon failure of the main control circuit to operate within a predetermined time period to cause closing of a dialysate operate valve and opening of a dialysate bypass valve and/or stopping of a blood pump when an aberrant condition in the dialysate conductivity, temperature, flow or negative pressure is sensed and/or when an aberrant condition in the arterial or venous blood pressure is sensed and/or excessive leakage of blood into the dialysate is sensed and said backup control circuit including control circuit means for controlling operation of said backup control circuit and having input contacts coupled to sensor inputs to the main control circuit, time delay circuit means having an input coupled to said control circuit means and operable to initiate a timing cycle for said predetermined time period upon receiving an error signal from said control circuit means, energizing and de-energizing circuit means having an input coupled to an output of said time delay circuit means and having outputs coupled to points in the main control circuit associated with coils for the dialysate operate valve solenoid, the dialysate bypass valve solenoid, and the blood pump relay and operable upon receiving an operate signal, after said predetermined time period has occurred and the main control circuit has not functioned properly, to close the operate valve, open the bypass valve and stop the blood pump.

BRIEF DESCRIPTIONS OF THE DRAWINGS

FIG. 1A and FIG. 1B taken together are a schematic circuit diagram of a control circuit for a modular proportioning kidney dialysis machine.

FIG. 2 is a backup control circuit adapted to be connected into the main control circuit shown in FIGS. 1A and 1B.

DESCRIPTION OF THE PREFERRED EMBODIMENT

Figure 1A:
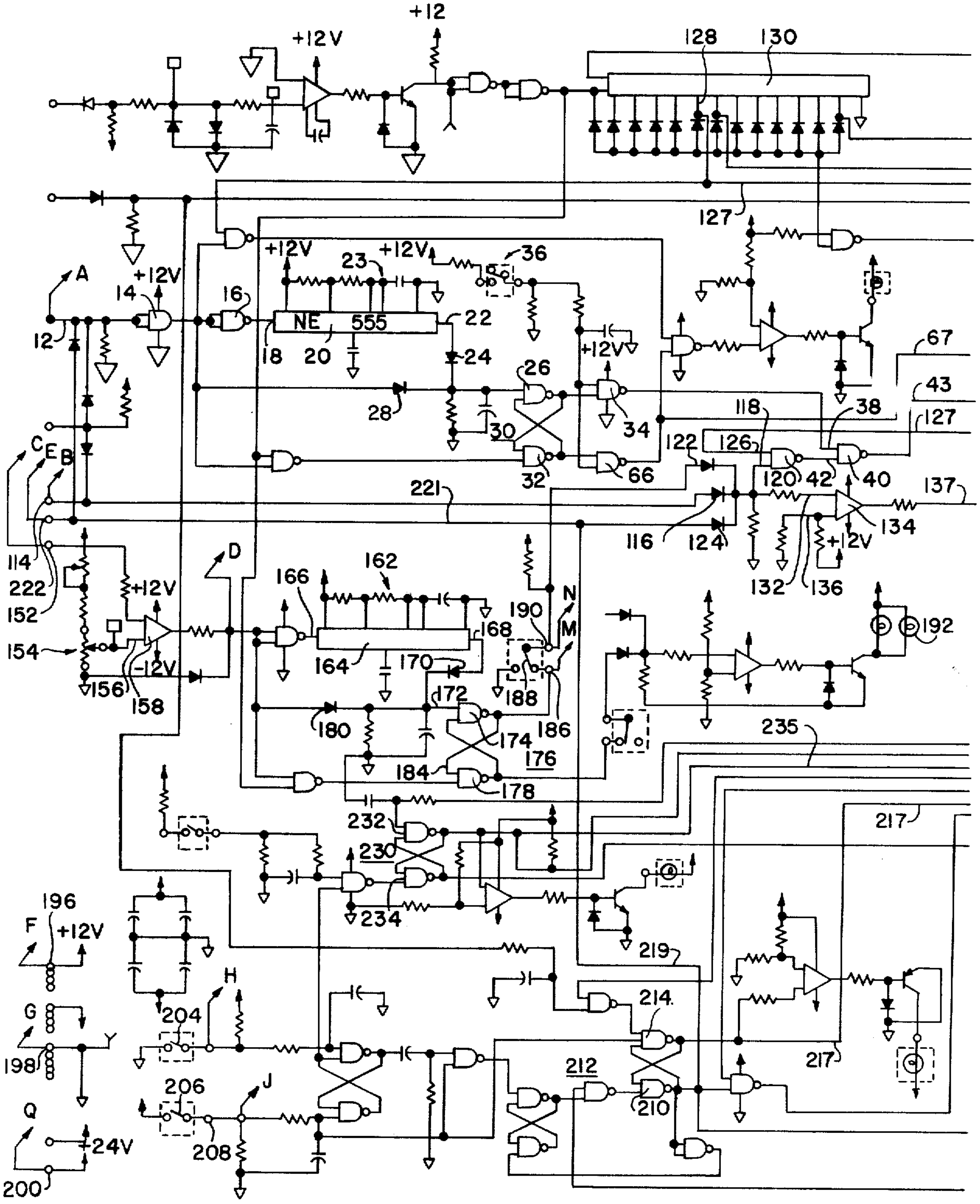
Figure 1B:
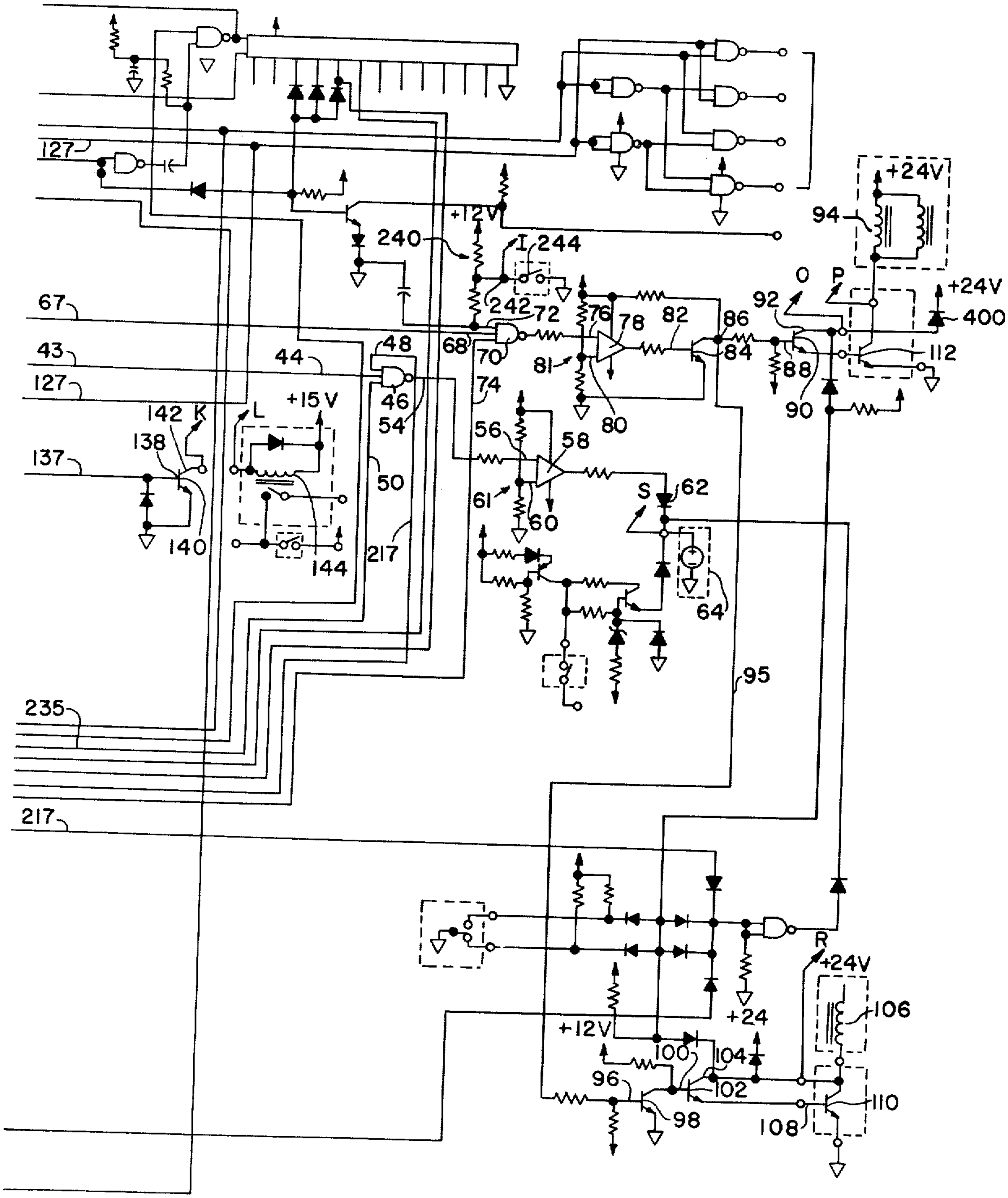

Referring now to the drawings in greater detail, there is illustrated in FIGS. 1A and 1B a schematic circuit diagram for a main control circuit for a kidney dialysis machine which is a modular proportioning machine.

In a kidney dialysis machine, a patient's blood is passed through a chamber having a membrane therein and having dialysate on the other side of the membrane. The membrane is pervious and allows impurities from the blood to pass through the membrane and be picked up by the dialysate. The cleansed blood is then returned to the patient.

In the operation of such a kidney dialysis machine it is important to monitor the temperature of the dialysate, the conductivity of the dialysate, the flow of the dialysate and the pressure of the dialysate. Also, it is important to monitor the amount of blood that leaks through the membrane into the dialysate. Accordingly, a kidney dialysis machine of the modular proportioning type has associated therewith a main control circuit of the type illustrated in FIGS. 1A and 1B which functions not only to control operation of the dialysis machine but also to monitor the various parameters of temperature, conductivity, flow and negative pressure of the dialysate and also blood leakage into the dialysate. For example, the temperature may be set at 36° and the control circuit is set so that if the temperature goes above 38° or below 34°, an alarm goes off.

Looking at FIG 1A, the sensor for sensing the temperature is connected to pin 12 of the main control circuit. This pin 12 is also connected to a conductivity sensor and normally has a low logic signal thereon. When the conductivity is out of range or when the temperature is out of range, the voltage level on pin 12 will go high. When there is an error condition, such as the temperature being out of limits or the conductivity being out of limits, the voltage on pin 12 goes high and this voltage is supplied to a NAND circuit 14. The output of the NAND circuit 14 is normally high and is applied to another NAND circuit 16 whose output is normally low. Now when the input to the NAND circuit 14 goes from low to high, that causes the output of the NAND circuit 16 to go from low to high and this change in signal level is applied to an input 18 of an integrated circuit timer 20 known under the code number NE 555. The integrated circuit timer 20 together with the resistors and capacitor connected thereto, form a five-second delay circuit 23. An output 22 of the integrated circuit timer is connected to a diode 24 to a NAND circuit 26. The output of the NAND circuit 14 is also coupled through a diode 28 to the input of the NAND circuit 26 which forms part of a bistable multivibrator (flip-flop) 30 with a NAND circuit 32.

The output of the NAND circuit 26 is normally low and the output of the NAND circuit 32 is normally high. It will be appreciated that when the normally low output of the NAND circuit 16 goes high for at least five seconds, the normally low output at the output 22 of the integrated timer circuit 20 will go high. This will result in the normally low output of the NAND circuit 26 going high. This high is then applied to a NAND circuit 34 which also has an input through a switch 36 which is normally closed. The output of the NAND circuit 34 is normally high. However, when either one of the inputs thereto goes high, it changes to low. It is apparent that the output from the NAND circuit 34 is connected to one input 38 of another NAND circuit 40. This NAND circuit 40 also has a second input 42 which is normally high. The logic level on the other input 42 will change depending upon other alarms that may occur and this will be described in greater detail hereinafter. At this point for a conductivity or temperature alarm, the input at 42 is normally high and when the input at 38 goes from a normal high to a low, the output of the NAND circuit 40 goes from a normally low to a high logic level.

The normally low output from the NAND circuit 40 is coupled by a conductor 43 to a middle input 44 of another NAND circuit 46. The NAND circuit 46 also has an input 48 and an input 50. The logic signal on the input 48 is normally high and the logic signal on input 50 is normally high for reasons which will be described in greater detail hereinafter. In any event, with a normally low signal level on the input 44, the output of the NAND circuit 46 is normally high. However, after five seconds of an error alarm, the signal level at the input 44 goes high so that all three inputs 44, 48 and 50 are high and the output 54 of the NAND circuit 46 goes from a normally high to a low.

The output 54 from the NAND circuit 46 is connected to one input 56 of a comparator 58. Another input 60 of the comparator 58 is connected to a voltage divider circuit 61, such that when there is a normally high signal level at the input 56, the output of the comparator 58 is in negative saturation and normally low. The highs at the input 56 and at the input 60 of the comparator 58 drive the comparator 58 into negative saturation such that there is a normal low or negative voltage output from the comparator 58 which is applied through a diode 62 to a Sonalert$_{TM}$ device 64.

Now, when the normally high signal level at the input 56 goes low, the comparator 58 is driven into positive saturation and a voltage is applied to the Sonalert$_{TM}$ 64 to cause the generation of an alarm sound such as a buzzing or horn sound. Also, a light is lit up on a control panel indicating that the conductivity or temperature is not within proper limits.

Additionally, the input pin 12 is connected to sensors which monitor the flow of dialysate and the negative pressure of the dialysate so that if either the flow or negative pressure are out of range, the voltage level at pin 12 will go high and in the manner described above, cause the Sonalert$_{TM}$ device 64 to produce an audio alarm to indicate an error condition.

Summarizing the above, pin 12 is connected to dialysate sensors which sense the temperature of the dialysate, the flow of the dialysate, the conductivity of the dialysate which is a salt solution, and the negative pressure of the dialysate. With respect to the latter, the dialysate must be under a slight negative pressure so that impurities pass from the blood through the membrane into the dialysate. Whenever any one of these parameters is out of limits, this is sensed by a sensor which then changes the voltage level on the pin 12 from a low to a high to cause the generation of an audio alarm from the device 64.

Also at the same time, when the output of the NAND circuit 32 goes from a normally high to a normally low, this changes the normally low output from a NAND circuit 66, which signal level is applied via conductor 67 to a middle input 68 of a NAND circuit 70. Another input 72 to the NAND circuit 70 has a normally high signal level from a plus twelve volts voltage source. A third input 74 to the NAND circuit 70 also has a normally high voltage level for reasons to be described hereinafter.

With inputs 72 and 74 normally being high and with input 68 normally being low, there is normally a high output from the NAND circuit 70 which is applied to one input 76 of a comparator 78 which has another input 80 coupled to a voltage divider circuit 81. With this arrangement, the voltage at the input 76 is approximately twice the voltage at the input 80, the respective voltages being approximately twelve volts and six volts. In this way, the comparator 78 is driven into negative saturation so as to apply a negative voltage to a base 82 of a transistor 84 so that the transistor 84 is normally turned off. In this way, a collector 86 of the transistor 84 is normally at a high voltage and this high voltage is applied to a base 88 of a transistor 90 so that the transistor 90 is normally on and the voltage at a collector 92 thereof is normally at zero volts so that a full twenty four volts is applied across a solenoid valve coil 94 of an operate valve which is coupled through the backup control circuit to be described hereinafter to the collector 92 of the transistor 90 to maintain the operate valve (not shown) in an open condition.

Now when the voltage at the input 68 of the NAND circuit 70 changes from a normally low to a normally high state as a result of a dialysate alarm condition occurring, all three inputs to the NAND circuit 70 are high resulting in the normally high output therefrom to change to a low. This low output is applied to the input 76 of the comparator 78 and drives same into positive saturation so that positive voltage is applied to the base 82 of the transistor 84 and turns the transistor 84 on. This causes the collector 86 of the transistor 84 to go low and this low voltage applied to the base 88 of the transistor 90 turns off the transistor 90 and this causes the solenoid valve coil 94 to be de-energized so as to shut off the operate valve.

At the same time the voltage at the collector 86 going from a high to a low is applied via a conductor 95 to a base 96 of a transistor 98 to turn off the transistor 98. This results in a plus twelve volts being applied to a base 100 of a transistor 102 which is normally not conducting. When the transistor 102 is not conducting, the collector 104 thereof is at twenty four volts such that there is no voltage drop across a solenoid valve coil 106 for a bypass valve (not shown). The bypass valve is normally in a closed position and is only opened when the operate valve is closed. When the transistor 102 is turned on, that allows voltage to be applied through the transistor 102 to a base 108 of a transistor 110 which is compound connected or Darlington paired with the transistor 102 much the same way that the transistor 90 is connected to a transistor 112 in the control circuit for the solenoid valve coil 94 for the operate valve. When the transistor 110 is turned on, there is immediately a voltage drop of twenty four volts across the solenoid valve coil 106 to operate the bypass valve.

From the foregoing description it will be apparent that when there is a dialysate alarm condition, the Sonalert$_{TM}$ device 64 is operated to provide a constant buzzing sound, the operate valve solenoid coil 94 is de-energized to close the operate valve and the bypass valve solenoid coil 106 is energized to open the bypass valve for the dialysate.

Returning to FIG. 1A, an input pin 114 is a blood pressure alarm pin which is normally low and goes high whenever a sensor associated with the venous flow senses a pressure which is outside a chosen range of pressure for venous pressure or when a sensor associated with the arterial flow senses a pressure outside a chosen range for arterial pressure. When this occurs, the high voltage on pin 114 is transmitted through a diode 116 to one input 118 of a NAND circuit 120. It is noted that there are two other diodes 122 and 124 which are also coupled to the input 118. The signal level applied to these diodes is a normally low signal as will be described in greater detail hereinafter. In any event, with three low signal levels applied to the input 118, the output of the NAND circuit 120 is normally high. As shown, the NAND circuit 120 has another input 126 which is connected via a conductor 127 to an input pin 128 of a CMOS counter 130 sold under the code number 14040. The counter 130 is operative to generate a pulse which has a fifty percent duty cycle at the pin 128. In other words, the pulse at the pin 128 is high and low for equal amounts of time with a period of ½ second and this signal is applied to the input 126 of the NAND circuit 120.

Now, when there is a blood pressure alarm on the pin 114 and the signal level thereon goes from low to high, this results in a high level signal being applied to the input 118 of the NAND circuit 120 while the high, low, high, low intermittent signal is applied to the input 126 of the NAND circuit 120. This results in low, high, low, high signal at the output of the NAND circuit 120 which is connected to the input 42 of the NAND circuit 40.

As described previously, the output from the NAND circuit 34 is normally high and this normally high signal level is applied to the other input 38 of the NAND circuit 40 so that there is a normally low output signal from the NAND circuit 40. Now, however, when the high signal level has been applied to the input 118 of the NAND circuit 120, the output of the NAND circuit 40 is a pulsating low, high, low, high signal with a fifty percent duty cycle. This signal is applied over conductor 43 to the NAND circuit 46 which results in a high, low, high, low intermittent signal at the output 54 from the NAND circuit 46 which then causes the output of the comparator 58 to go from negative saturation to positive saturation to negative saturation to positive saturation, etc., intermittently so that the Sonalert$_{TM}$ device 64 produces a regular beep, beep, beep signal. This will indicate to an operator of the kidney dialysis machine that there is an error condition in the blood circuit which could be either a blood pressure alarm as described above or a blood leak alarm into the dialysate as will be discussed hereinafter.

At the same time, the high signal that passes through the diode 116 to the input 118 of the NAND circuit 120 is also applied to one input 132 of a comparator 134 which has another input 136 connected to plus twelve volts. With a normally low signal applied to the input 132, the output of the comparator 134 is normally high so that this output applied via conductor 137 to a base 138 of a transistor 140 normally maintains the transistor 140 in an on condition. The transistor 140 has its collector 142 connected through the backup control circuit (250) to be described hereinafter to a relay coil 144 for operating a blood pump. With the transistor 140 conducting, fifteen volts is applied across the coil 144 to turn on the blood pump and operate the blood pump. However, when the normally low signal level applied to the input 132 of the comparator 134 is changed to a high input level, the output of the comparator 134 goes from positive saturation to negative saturation and the transistor 140 is then turned off causing de-energization of the relay coil 144 and stopping of the blood pump.

A pin 152 is connected to an optical sensor in a drain from the dialysate chamber in the kidney dialysis machine. This sensor is operable to sense the changes in optical density of the dialysate when blood is present in the dialysate. Since there is always some leakage of blood into the dialysate, the control circuit for monitoring blood leakage into the dialysate is designed to operate only when the blood leakage reaches a certain level. This level can be set on a voltage divider 154 which has an adjustable contact connected to one input 156 of a comparator 158, the other input 160 of which is connected to the pin 152. Typically, the adjustable contact of the voltage divider is set between zero and four volts so that the output of the comparator 158 does not change until the voltage at the pin 152 exceeds the voltage on the adjustable contact of the voltage divider 154. For example, the voltage input at the input 156 from the comparator 158 can be set at four volts and when the voltage on the pin 152 exceeds four volts, the normally positive voltage saturation at the output of the comparator 158 goes to negative saturation. This voltage output from the comparator 158 is applied to a time delay circuit 162 which includes an NE555 timer circuit 164. The voltage applied to an input 166 of the timer circuit 164 from the comparator 158 is normally low and goes high when the voltage at pin 152 exceeds four volts. Then a 3.5 second delay is provided by the timer circuit 164 so that the normally high level at output 168 will go low after 3.5 seconds. This voltage level from the output 168 is applied through a diode 170 to an input 172 of a NAND circuit 174 forming part of a bistable multivibrator (flip-flop) 176 with another NAND circuit 178. Also, it will be seen that the output from the comparator 158 is applied through another diode 180 to the input 172. Thus, when the normally high output from the comparator 158 goes low, this low is applied to the input of the diode 180. Meanwhile, however, the high at the output 168 of the timer circuit 164 is being applied through the diode 170 to the input 172 to maintain a high signal level at the input 172 of the NAND circuit 174. In the meantime, the low output from the NAND circuit 174 is supplied to an input 184 of the NAND circuit 178 to maintain a normally high output at the output of the NAND circuit 178. The normally low output from the NAND circuit 174 is applied to a pin 186 connected to one side of an override switch 188. Another pin 190 is connected to the other side of the override switch 188 and this switch is normally closed as shown.

It will be apparent that the pin 190 is coupled to the anode of the diode 122 and there is normally a low level signal on the diode 122 and there is normally a low level signal on the anode of the diode 122. However, the normally low output from the NAND circuit 174 is changed to a high output when a blood leak has been sensed above a certain level and 3.5 seconds have elapsed. This high output is then passed through the diode 122 to the input 118 of the NAND circuit 120. In this condition and as described above, with a high level signal on the input 118 of the NAND circuit 120 and an alternating high, low signal on the input 126, a low, high output from the NAND circuit 120 results in an intermittent low, high, low, high voltage being applied to the Sonalert$_{TM}$ device 64 to cause a beep, beep sound. Again it is noted that the intermittent high, low, high, low signal has a fifty percent duty cycle so that it is an on beep, off, on beep, off signal.

At the same time and in a conventional manner, the change of the normally high output from the NAND circuit 178 to a low output will cause energization of a blood leak alarm light 192 to indicate to the operator that the beeping is as a result of a blood leak above a certain level that had been preset with the comparator 154. In this way the operator will know that the beep, beep, beep sound is for a blood leak and not a blood pressure alarm.

The main control circuit for the kidney dialysis machine described above is conventional and forms no part of the present invention. Accordingly, a detailed description of all the components thereof is omitted except for a few additional portions of the circuit to be described below. Also, with the circuit components and their connections clearly illustrated in FIGS. 1A and 1B, one skilled in the art can easily discern the operation and purpose of these various circuit components and their interconnections.

Figure 2:
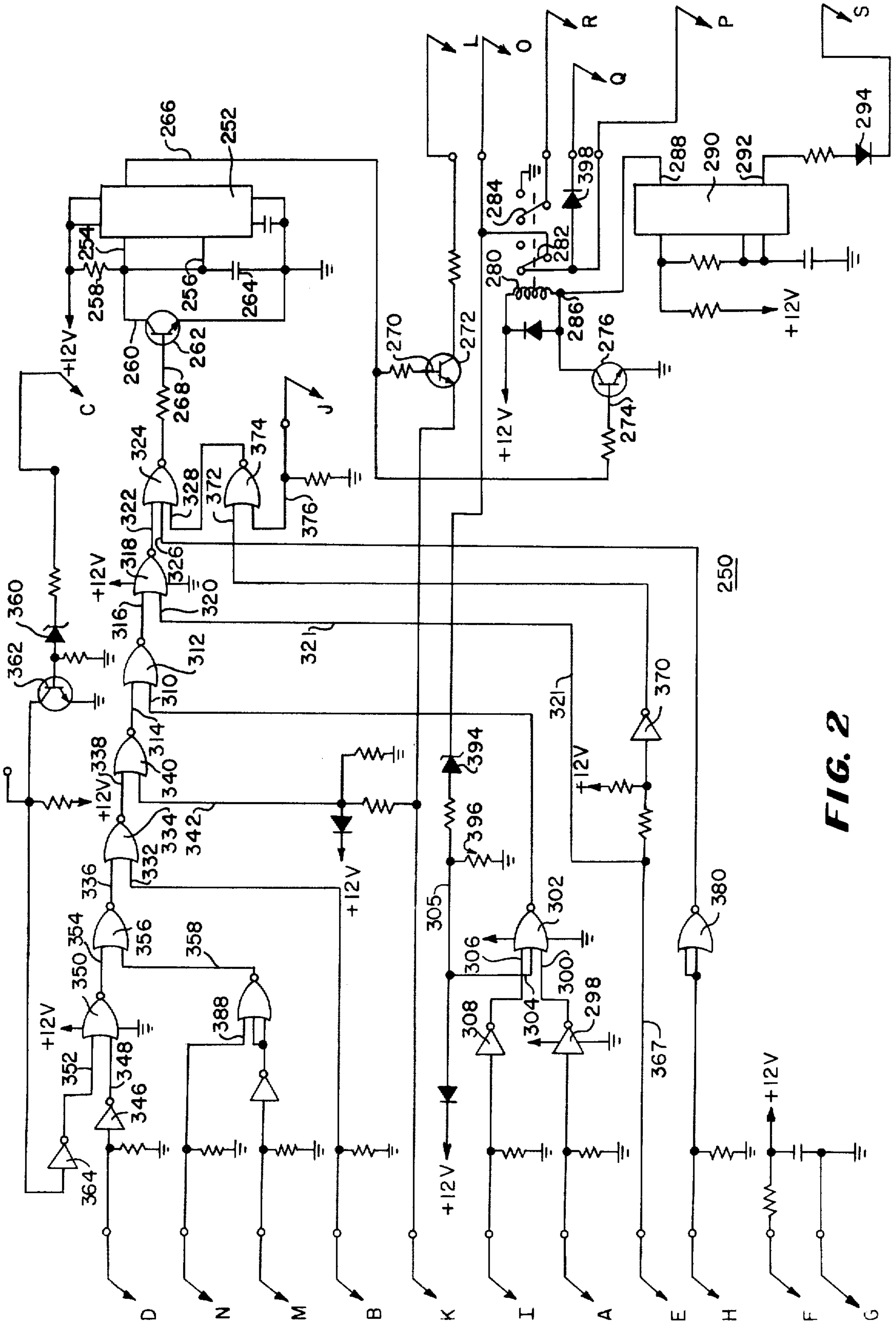

In any event, other parts and components of the circuit which will be referred to in connection with the description of the backup control circuit shown in FIG. 2 are now described below.

As shown, a pin 196 is connected to plus twelve volts. Another pin 198 is connected to system ground and a still further pin 200 is connected to plus twenty four volts.

A pin 202 is connected to one side of a clean switch 204 which is operated simultaneously with an interlock switch 206. A pin 208 is connected to one side of the interlock switch as shown. Without going into a lengthy explanation, it is to be understood that the output of a NAND circuit 210 forming part of a bistable multivibrator 212 with another NAND circuit 214 has a normally low output while the output of the NAND circuit 214 is normally high. The normally high output from the NAND circuit 214 is transmitted via a conductor 217 to the input 48 of the NAND circuit 46. If there is a failure in the components connected between the switches 204, 206 and the multivibrator 212, this will result in a change in the output levels of the NAND circuits 210 and 214 causing the voltage level at the input 48 to go from a low to a high and this high is communicated by a conductor 219 to another conductor 221 which is connected to an input pin 222 which is the pin for the sterilize mode of operation of the main control circuit of the kidney dialysis machine.

When it is desired to clean the machine and sterilize it, a bar must be moved on the machine which will then close both the interlock switch 206 and the clean switch 204. This will then change the voltage level at the output of the NAND circuit 210 from a low to a high and this high voltage level is transmitted via conductor 219 and the conductor 221 to the diode 124. This high voltage will cause the machine to operate in the clean mode for approximately 36 minutes. The bypass valve coil 106 is energized and the operate valve coil 94 is de-energized for the first 18 minutes and vice versa for the last 18 minutes. The machine will return to the normal operation mode at the end of the clean mode. The Sonalert$_{TM}$ 64 is off and the relay coil 144 is de-energized, hence the blood pump is stopped, during the entire 36 minute clean time.

Another bistable multivibrator (flip-flop) 230 comprised of a NAND circuit 232 and a NAND circuit 234 has a normally high voltage level at the output of the NAND circuit 232 which is applied via a conductor 235 to the input 50 of the NAND circuit 46.

Also as shown, the input 72 to the NAND circuit 70 has a voltage divider 240 connected thereto between the input 72 and plus twelve volts. A tap between two resistors of the voltage divider 240 is connected to a pin 242 which is connected to one side of a purge switch 244, the other side of the purge switch 244 being connected to system ground as shown. When it is desired to purge the system, the switch 244 is depressed connecting one half of the voltage divider to ground and thereby changing the normally high input voltage at the input 72 to a low input. When the voltage level at the input 72 goes from high to low on operation of the purge switch 244, the operate valve coil 94 is energized to open the operate valve and, of course, the bypass valve is then closed.

The main control circuit, and particularly the portions thereof just described above, is very effective in controlling the operation of a modular proportioning kidney dialysis machine. More specifically, the control circuit is very effective in causing the blood pump to be stopped and/or the operate valve to be closed and the bypass valve to be opened when there is an aberrant operating condition such as the arterial or venous blood pressure being outside of predetermined limits or excessive blood leakage into the dialysate and/or the operating parameters of the dialysate (conductivity, temperature, flow, negative pressure) being outside of predetermined limits. Also, when there is an aberrant condition, the override switch 188 can be operated to maintain the blood pump relay energized to pump the blood back into the patient.

However, it is always possible that a component of the circuit such as a resistor, capacitor, transistor or integrated circuit (IC) may fail and as a result the control circuit may not function in the manner described above. Also, to provide greater insurance against failure by utilizing very high reliability components in the circuit would be economically prohibitive. Accordingly, it is desirable that some circuit means be provided to ensure very, very high reliability of the control circuit in the event there is a component failure in any one of components in the main control circuit described above. According to the teachings of the present invention, such a circuit is provided by a backup control circuit 250 illustrated in FIG. 2. This backup control circuit 250 and its connections to the main control circuit shown in FIGS. 1A and 1B will now be described in detail in connection with the description of FIG. 2.

As shown, the backup control circuit 250 has a number of contact pins which are designated by alphabetical characters and which are adapted to connect with mating contacts also designated by the same alphabetical characters in the main control circuit shown in FIGS. 1A and 1B. These contacts and their interconnection with the main control circuit will now be described as follows. First of all, contact A is connected to input pin 12 which is connected to the sensor for dialysate conductivity, temperature, flow and negative pressure.

The contact B is connected to the blood pressure alarm pin 114 as shown in FIG. 1A. The contact C is connected to the blood leak pin 152. The contact D is connected on the other side of the blood leak comparator 158 to the output of the comparator 158 as shown in FIG. 1A. Contact E is connected to the sterilize pin 222. Contact F is connected to the plus twelve volt pin 196. Contact G is connected to system ground pin 198. Contact H is connected to pin 202 on the other side of the clean switch 204. Contact J is connected to the pin 208 of the interlock switch 206. Contact I is connected to the pin 242 of the purge switch 244. Contact K is connected to the collector 142 of transistor 140 and contact L is connected to the negative side of the blood pump relay coil 144. Contact M is connected to the pin 186 on one side of the override switch 188 and contact N is connected to pin 190 of the override switch 188. Contact O is connected to the collector 92 of the transistor 90 and contact P is connected to the negative side of the operate valve coil 94. Contact Q is connected to the plus twenty four volt pin 200. Contact R is connected to the collector 104 of the transistor 102 in the bypass valve circuit and contact S is connected to the cathode of the diode 62 which is connected to the input to the Sonalert$_{TM}$ device 64.

Before describing the component parts of the backup control circuit 250, it is important to note that the circuit between contacts K and L complete a circuit between the collector 142 of transistor 140 and the relay coil 144. Also, the contacts O and P complete a circuit between the collector 92 of the transistor 90 and the operate valve coil 94. Additionally it is noted that the contacts N and M are connected to opposite sides of the override switch 188.

As shown in FIG. 2, the backup control circuit 250 includes a time delay circuit 252 which has interconnected inputs 254, 256 and an output 266. As shown, a resistor 258 is connected between the plus twelve volt source and the input 254 as well as to a collector 260 of a transistor 262. This input 254 is also connected to one side of a capacitor 264, the other side of which is connected to system ground. The time delay circuit 252 also has an output 266. As will be described in greater detail hereinafter, the control circuit 250 is, in its normal state, applying a voltage to a base 268 of the transistor 262. As a result, the transistor 262 is normally on and conducting so that the capacitor 264 is shorted by the transistor 262 and is in a discharged state.

As will be explained in greater detail hereinafter, when there is an aberrant condition with the dialysate or with the blood, the transistor 262 is turned off to allow the capacitor 264 to charge. After a period of 10 seconds the capacitor 264 will charge to a voltage value at the input 256 which will trigger an output at the output 266. It will be remembered that normally the main control circuit will react to an aberrant condition after either five seconds or 3.5 seconds. However, if it should not act to close the operate valve, open the bypass valve and/or stop the blood pump, the backup control circuit 250 will then function in a manner to be described below to take over control of the kidney dialysis machine and cause the required functions to take place. In this respect, it will ensure that the operate valve is closed, the bypass valve is opened and/or the blood pump is stopped.

In the operation of the control circuit 250 after 10 seconds have elapsed and the main control circuit has not functioned properly a normally high voltage at the output 266 is changed to a low voltage which is applied to a base 270 of a transistor 272 and to a base 274 of a transistor 276.

As described above, the output 266 is normally high so that the transistor 272 is normally on to complete a circuit from contact L to contact K which completes a circuit from the blood pump relay 144 to the collector 142 of transistor 140. Thus it will be seen that when the backup control circuit 250 takes over, it immediately opens the circuit to the blood pump relay coil 144 to stop the blood pump.

At the same time the normally high voltage applied to the base 274 to maintain the transistor 276 on is changed to a low to turn off the transistor 276 which is connected in series with a relay coil 280 which is maintaining a relay contact 282 in the closed position as shown and another relay contact 284 in the open position as shown. However, when the transistor 276 is turned off, the relay contact 282 is moved from a closed position to an open position and this results in creating an open circuit between contacts O and P which had up to this point in time been maintaining a closed circuit between the collector 92 of the transistor 90 and the operate valve coil 94. As a result, the operate valve coil 94 is de-energized and the operate valve is closed. At the same time the open circuit to contact R is connected between plus twenty four volts and ground to energize same and open the bypass valve.

Also at the same time a negative side 286 of the relay coil 280 goes from a low near ground potential to a high of plus twelve volts which is applied to an input 288 of an oscillator circuit 290. In its normal quiescent state, the oscillator 290 with a low voltage input at input 288 produces no signal at an output 292 thereof. However, when the voltage level at the input 288 goes from a low to a high, the oscillator then generates an oscillating signal having an eighty percent duty cycle at the output 292. This eighty percent duty cycle means that a high voltage signal is generated for eighty percent of the cycle and a zero voltage is generated for twenty percent of the cycle. This eighty percent duty cycle pulse is then applied through a diode 294 to the contact S which delivers this pulse to the input of the Sonalert$_{TM}$ device 64 to cause the same to make a beeeep, beeeep, beeeep sound. This sound is different from the beep, beep, beep sound caused when there is a blood leak or a blood pressure alarm and indicates to an operator that the backup control circuit has taken over control of the kidney dialysis machine. In this way the operator is alerted to the fact that there has been a failure in the main control circuit.

The manner in which the transistor 262 is turned off as a result of the backup control circuit 250 picking up different signals at the inputs to the main control circuit will now be described below.

First of all when there is an aberrant condition in the dialysate such as temperature, conductivity, flow or negative pressure being out of range, the normally low voltage signal on the pin 12 which is applied through the A contact to the backup control circuit 250 is applied to the input of an inverting amplifier 298. The output of the inverting amplifier 298 is normally high and is applied to one input 300 of a NOR circuit 302 which also has a second input 304 connected to a conductor 305 and a third input 306 connected to the output of another inverting amplifier 308 which has its input connected to the pin 242 of the purge switch 244 through the I contact. As a result, before an error condition occurs, there is a normally high input to the inverting amplifier 308 which supplies a normally low voltage level to the input 306. At the same time, a normally low signal is applied from system ground through the conductor 305 to the input 304 of the NOR circuit 302. And, with a normally low input to the inverting amplifier 298, a normally high voltage level is applied to the input 300 of the NOR circuit 302. With a high at the input of 300, the output of NOR circuit 302 is normally low and is applied to one input 310 of a NOR circuit 312 which has another input 314 that has a normally low signal thereon as will be described hereinafter. As a result, the output from the NOR circuit 312 is normally high and is applied to an input 316 of another NOR circuit 318. The NOR circuit 318 has another input 320 which is connected by a conductor 321 through the E contact to the sterilize pin 222 which normally has a low level signal thereon. As a result of a high level signal on the input 316 and low level signal on the input 320, the output of the NOR circuit 318 is normally low and is applied to one input 322 of another NOR circuit 324. In other words, there is a normally low signal to the input 322.

The NOR circuit 324 has two other inputs 326 and 328 which also have a normally low input thereon as will be explained in greater detail hereinafter. As a result, with three low inputs to the NOR circuit 324, the output is normally high and this normally high output is applied to the base 268 of the transistor 262 to maintain the transistor 262 turned on.

Going back to the alarm condition which changes the input on contact A to the inverting amplifier 298 from a low to a high, the output thereon is changed from a high to a low and then with all the inputs to the NOR circuit 302 being low, the normally low output therefrom is changed to a high and this high is applied to the input 310 of the NOR circuit 312. As a result, the normally high output from the NOR circuit 312 is changed to a low and that results in two lows being applied to the inputs of the NOR circuit 318 to change the output therefrom from a normally low output to a high output. This high output is applied to the input 322 of the NOR circuit 324 to change the output therefrom from a high to a low thus turning off the transistor 262. If the main control circuit does not function to close the operate valve and open the bypass valve within ten seconds, the backup control circuit 250 will take over and cause this to happen in the manner described above.

Looking at FIGS. 1A and 2 it will be noted that the contact B is connected to the blood pressure input pin 114 which normally has a low level signal thereon until an error condition occurs in the blood pressure.

In the backup control circuit 250 the contact B is connected to an input 322 of a NOR circuit 334 which has another input 336 on which there is a normally low level signal. As a result, the output of the NOR circuit 334 is normally high and this high level signal is applied to the input 338 of another NOR circuit 340. This NOR circuit 340 has another input 342 on which there is a normally low level signal. As a result, the output of the NOR circuit 340 is normally low and is supplied to the input 314 of the NOR circuit 312 described above.

Now when an error condition occurs in the blood pressure being sensed and the signal level at the input pin 114 goes from low to high, this high applied to the input 332 of the NOR circuit 334 changes the output thereof from a high to a low. Then with two lows supplied to the inputs 338 and 342 of the NOR circuit 340, the output thereof changes from a low to a high. Then with a high and a low supplied to the inputs of the NOR circuit 312, the output thereof is changed from a high to a low. Then with two lows being applied to the NOR circuit 318 the output thereof changes from a low to a high. Continuing, the application of a high and two lows to the NOR circuit 324 then causes the NOR circuit 324 to change its output from a high to a low to turn off transistor 262 and start the capacitor 264 charging. Again, if after ten seconds the main control circuit has not operated, which control circuit should have operated within either 3.5 or five seconds, then the backup control circuit 250 will take over in the manner described above.

Looking at FIGS. 1A and 2 it will be apparent that contact C is connected to pin 152 which is the blood leak input pin. Also it is to be noted that contact D is connected to the output of the blood leak comparator 158. These two connections are made so that if there is any component failure in the voltage divider 154 or the comparator 158 and associated circuit elements, then the input at contact C will ensure that the backup control circuit 250 takes over. In any event, the input to the D contact of the backup control circuit 250 from the output of the comparator 158 is normally a high and goes to a low when a blood leak in excess of a certain amount is sensed. This causes the normally low output of an inverting amplifier 346 to go from low to high. The normally low output from the inverting amplifier 346 is applied to one input 348 of the NOR circuit 350. As will be described hereinafter, another input 352 of the NOR circuit 350 normally has a low signal level thereon. With two normally low inputs, the output of a NOR circuit 350 is normally high and this is supplied to an input 354 of another NOR circuit 356 which has another input 358 which has a normally low output. With a normally high signal level at the input 354 and a normally low signal level on the input 358 there is a normally low output from the NOR circuit 356 which is applied to the input 336 of the NOR circuit 334.

Now when the normally high input on the contact D supplied to the amplifier 346 is changed from high to low, the output from the amplifier 346 is changed from low to high. This results in the output of the NOR circuit 350 changing from a high to a low. This initiates a chain reaction of changes in outputs in the NOR circuits 356, 334, 340, 312, 318 and 324 in the manner described above to cause the output of the NOR circuit 324 to change from high to low to shut off transistor 262 so that the capacitor 264 can start charging.

At the same time, the out of range voltage level at the input pin 152 is supplied via the closed contact C through a Zener diode 360 to turn on a transistor 362 so that the collector thereof goes from a normally high to a normally low. This normally high signal level is supplied to an inverting amplifier 364 which provides a normally low signal level to the input 352 of the NOR circuit 350. However, when the transistor 362 is turned on, the voltage level signal at the input 352 is changed from a low to a high to ensure with one or two highs applied to the inputs of the NOR circuit 350, that the blood leak condition will be sensed so as to turn off transistor 262 and start charging capacitor 264.

Assuming there is a component failure in one of the NAND circuits between the clean and interlock switches 204 and 206 and the sterilize pin 22 such as, for example, in NAND circuit 210 causing the output of the NAND circuit 210 to go from low to high, this high would be supplied to the sterilize pin 222 which is connected to the E contact. This normally low signal is supplied via conductors 367 and 321 to the input 320 of the NOR circuit 318. However, when this signal level is changed from low to high, two highs are supplied to the NOR circuit 318 causing the output therefrom to maintain at low.

At the same time the normally low level signal on the contact E is supplied to an inverting amplifier 370 which has a normally high output that is supplied to an input 372 of a NOR circuit 374 which has another input 376. Following the connections, it will be apparent that there is a low level signal at the input 372 of the NOR circuit 374 and by reason of the J contact being connected to normally grounded pin 208 of the interlock switch 206, the voltage level at the input 376 is normally low. Since there are two lows at both inputs of the NOR circuit 374, the output of NOR circuit 374, or the input 328 of the NOR circuit 324 changes from normally low to high when pin 222 goes high and this causes the output of NOR circuit 324 to go low to turn off the transistor 262 and start the capacitor 264 charging.

When the purge switch 244 is operated, the high on contact I goes momentarily from a high to a low and then back to a high. However, if it stays low, that would change the output from the inverting amplifier 308 from a low to a high and this will maintain the output from the NOR circuit 302 at a low even though there is a dialysate alarm at contact A, i.e., a high signal at the input of the inverting amplifier 298. Hence a low signal then appears at the output of amplifier 298. This low signal is applied to the input 300 of the NOR circuit 302. Since the input 306 to NOR circuit 302 is high, the output of the NOR circuit 302 is maintained at low which is then applied to the NOR circuit 312 and this will result in the transistor 262 being turned on to ensure that the operate valve is opened and the bypass is closed at a dialysate alarm condition.

Contact H is connected to pin 202 of the clean switch which, when it is desired to clean the dialysis machine, is closed momentarily. This results in a normally high voltage level on the contact H going momentarily to a low and then back to a high. This is applied to a NOR circuit 380 which normally has a low output but which will have a momentarily high output when the clean switch 204 is operated. This results in a momentarily high voltage level at the input 326 of the NOR circuit 324. If this switch should be stuck, this high voltage remains on the input 326 to cause the transistor 262 to be turned off.

The contact N is connected to the pin 190 on one side of the override switch 188 and the contact M is connected to the pin 186 on the other side of the override switch 188. The override switch is normally closed as shown and the normally low output from the NAND circuit 174 is on both pins 186 and 190 so that contact M and N are normally low. However, when there is a blood leak, the output of the NAND circuit 174 goes from low to high and when the override switch 188 is depressed, this connects the contact N to low maintaining that contact low while at the same time the high output from the NAND circuit 174 is applied via the pin 186 to contact M. As shown in FIG. 2, with a normally low voltage level on the contact M, the output of an inverting amplifier 384 is normally high and this normally high voltage level is applied to two inputs of a NOR circuit 386. Another input 388 of the NOR circuit 386 is connected to the contact N and is normally low and stays low when the override switch is depressed. Thus, if there is a blood leak alarm condition and the override switch 188 is depressed, the signal level on contact N will be low and the signal level on contact M will be high and is changed to a low so that there are two lows going into the NOR circuit 386. This changes the normally low output from the NOR circuit 386 to a high which is then applied to the input 358 of the NOR circuit 356. With a high on the input 358 as a result of the override switch being depressed, and a low on the input 354 as a result of the blood leak alarm signal at contacts C and D, there will still be a normal low at the output of the NOR circuit 356 to prevent the transistor 262 from being turned off. In other words, the override for the main control circuit will also function to override the backup control circuit 250.

It is to be noted that when there is a dialysate alarm and a signal level on contact A goes from a low to a high, and the main control circuit works, we get a voltage level on contact O that goes from a low to a high. That high of twenty four volts will go through a Zener diode 394 and through a voltage divider circuit 396 to provide a positive voltage or high on the input 304 of the NOR circuit 302. In this respect, we normally have a low on input 306, a low on input 304 and a high on input 300. Now when the high on input 300 changes to a low as a result of a dialysate alarm, the operation of the main control circuit supplies a high via the Zener diode 396 to the input 304 so that we still have one high input to the NOR circuit 302 to maintain the normally low output. In this way, transistor 262 is maintained conducting and is not shut off.

At this point, if the operator needs to purge the machine when there is a dialysis alarm and the patient is not connected, then he will press the purge switch 244. That will result in a change on the contact I from high to low which causes the voltage level at the input 306 of the NOR circuit 302 to go from low to high. This also maintains a low on the output of the NOR circuit 302 and keeps the backup control circuit 250 from taking over operation of the dialysis machine.

Also, the Zener diode 394 prevents a short or ground on the negative side of the operate valve coil 94 from changing the normally low level on input 304 to a high level. Additionally, a diode 398 provides a path for a voltage surge such as caused by a ground or a short to the twenty four volt source on pin 200. The diode 398 is also used to provide a feed back path for any EMF generated in the operate valve coil 94 and this will work in the same way as a diode 400 coupled between contact O and the plus twenty four volt source in the main circuit.

From the foregoing description it will be apparent that the backup control circuit 250 of the present invention has a number of advantages some of which have been described above and others of which are inherent in the invention. Also it will be apparent that obvious modifications can be made to the specific components and their connections in the backup control circuit 250 without departing from the teachings of the invention. Accordingly, the present invention is only to be limited as necessitated by the scope of the accompanying claims.

We claim:

1. A backup control circuit for use with a main control circuit for a kidney dialysis machine, said backup control circuit being operable upon failure of the main control circuit to operate within a predetermined time period to cause closing of a dialysate operate valve and opening of a dialysate bypass valve or stopping of a blood pump when an aberrant condition in the dialysate conductivity, temperature, flow or negative pressure is sensed or when an aberrant condition in the arterial or venous blood pressure is sensed or excessive leakage of blood into the dialysate is sensed and said backup control circuit including control circuit means for controlling operation of said backup control circuit and having input contacts coupled to sensor inputs to the main control circuit, time delay circuit means having an input coupled to said control circuit means and operable to initiate a timing cycle for said predetermined time period upon receiving an error signal from said control circuit means, energizing and de-energizing circuit means having an input coupled to an output of said time delay circuit means and having outputs coupled to points in the main control circuit associated with coils for the dialysate operate valve, the dialysate bypass valve and the blood pump relay and operable upon receiving an operate signal, after said predetermined time period has occurred and the main control circuit has not functioned properly, to close the operate valve, open the bypass valve and stop the blood pump.

2. The backup control circuit according to claim 1 including an oscillator circuit coupled to the energizing and de-energizing circuit means and operable, upon energization of the deenergizing and energizing circuit means to generate an eighty percent on, twenty percent off duty cycle signal which is applied to an audio alarm device for generating a beeeep signal which is eighty percent on and twenty percent off during operation of said oscillator circuit.

3. The backup control circuit according to claim 1 wherein said time delay circuit means includes a multivibrator having at least one input and one output, a capacitor connected to at least one input and system ground, a resistor connected between said capacitor and system voltage and a normally conducting transistor across and shorting out said capacitor, a base of said transistor being coupled to the output of said control circuit means which normally supplied a bias voltage to said base to maintain said transistor conducting and shorting out said capacitor, and said capacitor having a charging constant through said resistor such that a voltage sufficient to trigger said multivibrator is not built up on such capacitor until said predetermined time period has occurred after said transistor is turned off by said control circuit means.

* * * * *